US00PP09506P

United States Patent [19]

Saville

[11] Patent Number: Plant 9,506

[45] Date of Patent: Apr. 16, 1996

[54] MINIATURE ROSE PLANT NAMED 'SAVABE'

[75] Inventor: F. Harmon Saville, Rowley, Mass.

[73] Assignee: Nor'East Miniature Roses, Inc., Rowley, Mass.

[21] Appl. No.: 364,591

[22] Filed: Dec. 27, 1994

[51] Int. Cl.[6] ..... A01H 5/00

[52] U.S. Cl. ..... Plt./8.2

[58] Field of Search ..... Plt./7.1, 8.2

*Primary Examiner*—Howard J. Locker

*Attorney, Agent, or Firm*—Christie, Parker & Hale

[57] ABSTRACT

A new miniature rose with yellow flowers of good form.

1 Drawing Sheet

SUMMARY OF THE INVENTION

The present invention relates to a new and distinct variety of rose plant of the miniature rose class, which was created by me by crossing as seed parent the variety known as 'Party Girl', U.S. Plant Pat. No. 4,598, and as pollen parent the variety known as 'Sonnenkind', also known by the cultivar designation 'Korhitom' and by the trade name Perestroika. The varietal denomination of this new rose is 'Savabe'.

Among the novel characteristics possessed by this new variety which distinguishes it from its parents and all other varieties of which I am aware is its attractive yellow flowers of good exhibition form.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—'Party Girl'.

*Pollen parent.*—'Sonnenkind'.

*Class.*—Miniature.

The following observations are made of specimens grown under glass in Essex County, Mass., during the month of July.

FLOWER

Blooming habit: Recurrent.

A. Bud:

(1) *Size.*—Small.

(2) *Form.*—Ovate, pointed.

(3) *Color.*—As sepals divide, bud color is near 14A.

(4) *Sepals.*—Slightly longer than bud, slight foliation, near 146B.

(5) *Peduncle.*—Length — about ½ to 1 inch. Aspect — straight. Strength — erect. Color — near 144A.

B. Bloom:

(1) *Size.*—Average size when fully expanded — about 1½ inches.

(2) *Borne.*—Singly and several together in small sprays, flower stem about 1 to 2 inches.

(3) *Form.*—High centered at first becoming flat, outer petals quill at maturity.

(4) *Petalage.*—Number of petals under normal conditions — about 22–30.

(5) *Color.*—During first two days, inner petals at center of flower near 15A; outer petals near 14A; base of petals at point of attachment near 14B; reverse of petals near 14C and general tonality from a distance is bright golden yellow. As bloom ages the color changes from near 15B to near 14B and then to near 14C, with outer petals being lighter in fully open blooms. Thereafter the color changes from near 14C to near 12C and ultimately to near 10D. After three or more days there is a mix of yellow colors.

C. Petals:

(1) Texture.—Thick, firm.

(2) *Appearance.*—Inside velvety and outside satiny.

(3) *Form.*—Fan-shaped.

(4) *Arrangement.*—Imbricated, regularly arranged, shingle-like.

(5) *Petaloids in center.*—Variable in number up to about 14.

(6) *Persistence.*—Average.

(7) *Fragrance.*—None.

(8) *Lasting quality.*—Up to about 22 days on the plant before petals drop and up to about 2 days after cutting.

REPRODUCTIVE ORGANS

A. Stamens, filaments and anthers:

*Arrangement and color.*—Regularly arranged around styles.

*Color.*—Near 10D.

B. Pollen:

*Color.*—Near 21A.

C. Styles: Uneven length, near 46B.

D. Stigmas:

*Color.*—Near 49B.

E. Hips: None observed.

PLANT

A. Form: Upright.

B. Growth: Very vigorous.

*Height attained.*—About 16 to 20 inches.

C. Foliage: Compound 5 to 7 leaflets.

(1) *Size.*—Small.

(2) *Quantity.*—Abundant.

(3) *Color.*—New foliage: Upper side — near 137B. Underside — near 138B. Old foliage: Upper side — near 147A. Underside — near 137C.

(4) *Shape.*—Oval, pointed.

(5) *Texture.*—Upper side is semi-glossy; underside is matte.

(6) *Edge.*—Serrated.

(7) *Serration.*—Serrate.

(8) *Leaf stem.*—Color — near 137C. Underside — 137D.

(9) *Stipules.*—Slight bearded.

(10) *Resistance to disease.*—Blackspot — average. Mildew — average. Rust — average.

D. Wood:

(1) *New wood.*—Color — near 137B. Bark — smooth.

(2) *Old wood.*—Color — near 137B. Bark — smooth.

E. Thorns:

*Quantity (main stalk).*—Very few.

*On laterals from stalk.*—Very few.

*Form.*—Long, thin, straight.

*Length.*—Short.

*Color.*—Near 144B.

*Position.*—Irregular.

*Prickles.*—None.

F. Winter hardiness: Needs protection in severe climates.

I claim:

1. A new and distinct variety of rose plant of the miniature rose class, substantially as shown and described.

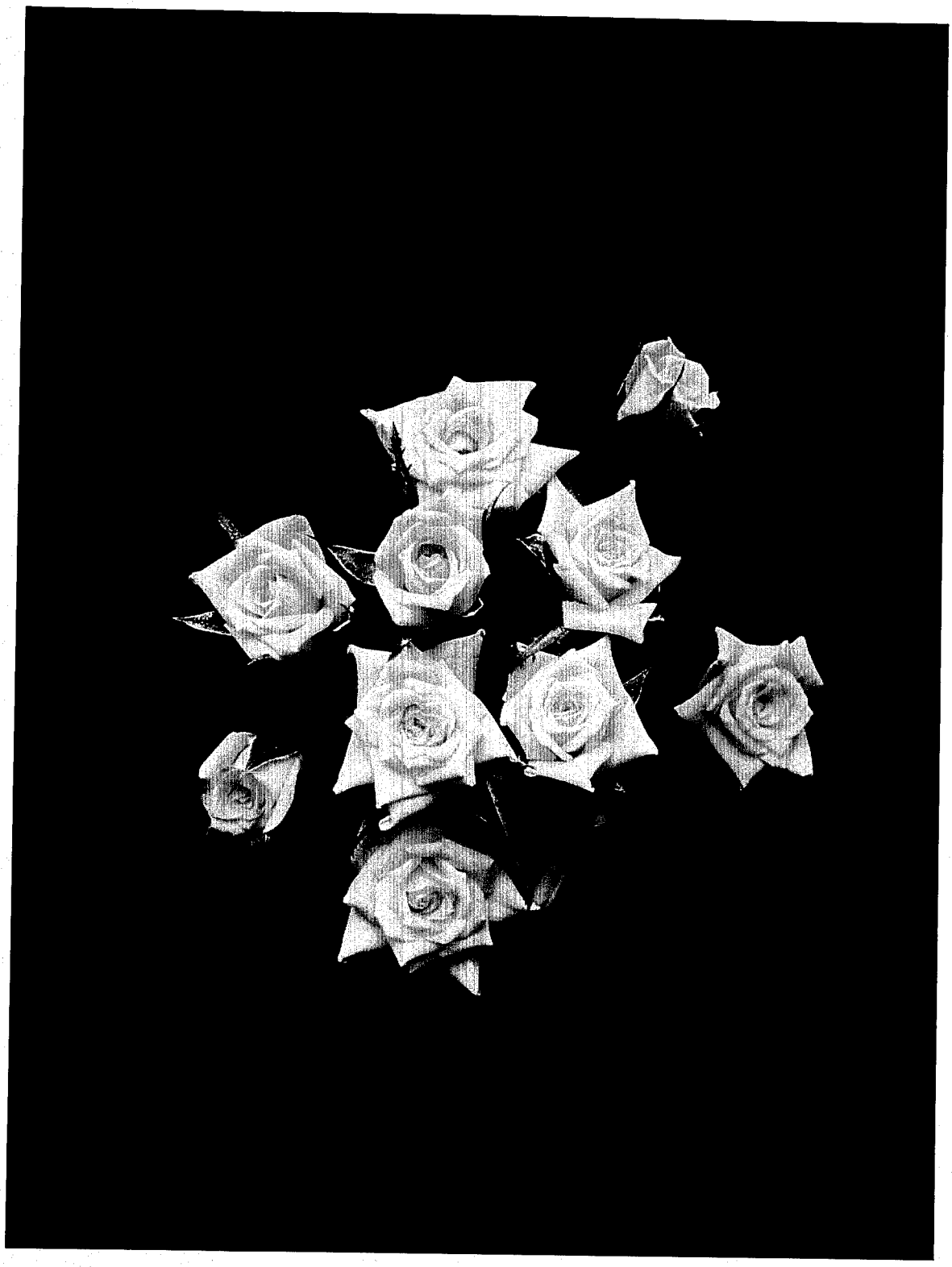

* * * * *